US005283340A

United States Patent [19]

Begley et al.

[11] Patent Number: 5,283,340

[45] Date of Patent: Feb. 1, 1994

[54] PHOTOGRAPHIC MATERIAL AND PROCESS COMPRISING WASH-OUT NAPHTHOLIC COUPLER

[75] Inventors: William J. Begley, Webster; Teh-hsuan Chen, Fairport; Hans G. Ling, Rochester; John W. Harder, Rochester; Arlyce T. Bowne, Rochester, all of N.Y.

[73] Assignee: Eastman Kodak Company, Rochester, N.Y.

[21] Appl. No.: 893,285

[22] Filed: Jun. 4, 1992

Related U.S. Application Data

[60] Division of Ser. No. 748,499, Aug. 22, 1992, Pat. No. 5,151,343, which is a continuation-in-part of Ser. No. 733,554, Jul. 22, 1991, Pat. No. 5,234,800.

[51] Int. Cl.[5] .................... C07D 271/10; C07D 257/04

[52] U.S. Cl. .................................... 548/144; 548/251; 548/187

[58] Field of Search ........................ 548/251, 144, 187

[56] References Cited

U.S. PATENT DOCUMENTS

| | | | |
|---|---|---|---|
| 3,227,550 | 1/1966 | Whitmore et al. | 430/226 |
| 3,227,554 | 1/1966 | Barr et al. | 430/542 |
| 3,458,315 | 7/1969 | Loria | 430/553 |
| 4,248,962 | 2/1981 | Lau | 430/382 |
| 4,409,323 | 10/1983 | Sato et al. | 430/544 |
| 4,482,629 | 11/1984 | Nakagawa et al. | 430/542 |
| 4,847,185 | 7/1989 | Begley et al. | 430/376 |
| 4,857,440 | 8/1989 | Begley et al. | 430/382 |
| 4,857,447 | 8/1989 | Tamoto et al. | 430/544 |
| 4,861,701 | 8/1989 | Burns et al. | 430/543 |
| 5,021,322 | 6/1991 | Begley et al. | 430/223 |
| 5,026,618 | 6/1991 | Begley et al. | 430/382 |
| 5,026,628 | 6/1991 | Begley | 430/382 |

FOREIGN PATENT DOCUMENTS

| | | |
|---|---|---|
| 443530 | 8/1991 | European Pat. Off. . |
| 2462184 | 3/1976 | Fed. Rep. of Germany . |
| 2543014 | 4/1976 | Fed. Rep. of Germany . |
| 79-674119 | 5/1979 | Japan . |
| 59-162545 | 9/1984 | Japan . |

OTHER PUBLICATIONS

"The Theory Of The Photographic Process", 4th Edition , Edited By T. H. James, 1977, pp. 359-361.

Research Disclosure, Dec. 1989, Item #308119.

*Primary Examiner*—Robert Gerstl
*Attorney, Agent, or Firm*—Arthur E. Kluegel

[57] ABSTRACT

A photographic naphtholic coupler comprising a ballast free naphtholic coupler moiety containing a —$CONH_2$ group in the 2- position and a ballasted coupling-off group in the 4- position enables good wash out of dye formed upon oxidative coupling from a photographic material during processing of such a photographic material. Such a naphtholic coupler is useful in photographic silver halide materials and processes.

4 Claims, No Drawings

PHOTOGRAPHIC MATERIAL AND PROCESS COMPRISING WASH-OUT NAPHTHOLIC COUPLER

This is a divisional of application Ser. No. 07/748,499, filed Aug. 22, 1992, now U.S. Pat. No. 5,151,343, which is a continuation-in-part of Ser. No. 733,554, filed Jul. 22, 1991, now U.S. Pat. No. 5,234,800.

This invention relates to a new photographic naphtholic coupler capable upon oxidative coupling of forming a dye that is capable of being washed out of the photographic material containing the coupler upon processing and to photographic materials and processes comprising the naphtholic coupler.

Various couplers are known in photographic materials and processes. One of the classes of photographic couplers includes naphtholic couplers that typically form cyan dyes upon oxidative coupling in photographic materials and processes. These naphtholic couplers typically form cyan dyes upon oxidative coupling with color developing agents. Such naphtholic couplers are also known which are capable of forming dyes upon oxidative coupling that can be washed out of the photographic material upon processing. These naphtholic couplers are described in, for example, U.S. Pat. No. 4,482,629.

The naphtholic couplers that are capable of forming dyes that can be washed out of the photographic material upon photographic processing contain a water solubilizing group, such as a carboxy group or sulfonic acid group, substituted on a group in the 2- position of the naphtholic coupler. It has been desirable to provide a naphtholic coupler that is not as expensive to manufacture as the described naphtholic couplers and still provides a useful dye that can be washed out of the photographic material with the added advantage that the coupler enables a lower concentration of coupler to be used in a photographic element without significantly changing imaging results.

It has also been desirable to provide such a naphtholic coupler that contains a coupling-off group that enables desired acutance and desired interimage effects in a color photographic silver halide material and process at lower concentrations of coupler.

The present invention solves these problems by providing a photographic element comprising a support bearing at least one photographic silver halide emulsion layer and an immobile naphtholic coupler capable upon oxidative coupling of forming a dye that is capable of being washed out of the photographic element upon photographic processing, wherein the immobile naphtholic coupler comprises a ballast free naphtholic coupler moiety comprising a $-CONH_2$ group in the 2-position and a ballasted coupling-off group in the 4-position comprising a releasable development inhibitor group. The ballasted coupling-off group preferably comprises a releasable photographically useful group (PUG) that is a releasable development inhibitor group.

The immobile naphtholic coupler is typically represented by the formula:

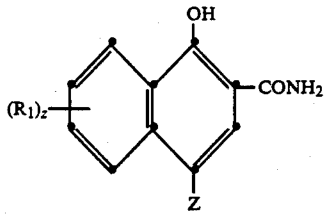

wherein Z is a ballasted coupling-off group that is a releasable development inhibitor group, $R_1$ is a ballast-free substituent that does not adversely affect the desired properties of the coupler and dye, and z is 0, 1, 2 or 3. $R_1$ does not comprise a ballast group because such a group adversely affects wash-out properties of the dye formed from the naphtholic coupler.

The ballasted coupling-off group (Z) enables the naphtholic coupler to be immobile in the photographic element prior to exposure and processing. Upon exposure and processing of the described element the naphtholic coupler reacts with oxidized color developing agent to form a dye that is washed out of the element during processing. Also, the coupling-off group is released during processing. The portion of the coupling-off group containing the ballast group remains in the location in which it was coated. The coupling-off group preferably comprises a releasable photographically useful group (PUG) which is released upon photographic processing. The PUG either is immobilized to remain in the location of the element in which it was coated or the PUG is mobile to allow it, after release, to move to a location in the element at which it can serve its intended function.

A preferred naphtholic coupler as described comprises a coupling-off group represented by the formula:

$$-(LINK)_n-(TIME)_m-PUG$$

wherein

- TIME is a releasable timing group capable of being released from the LINK moiety during photographic processing;
- LINK is a releasable linking group capable of being released from the naphtholic coupler moiety upon oxidative coupling of the naphtholic coupler;
- n and m individually are 0, 1 or 2;
- PUG is a releasable photographically useful group that is a releasable development inhibitor group; and, preferably,
- at least one of n and m is 1 or 2.

A process of forming an image having the described advantages comprises developing an exposed photographic element as described by means of a color developing agent in the presence of the described naphtholic coupler and washing-out the dye formed from the naphtholic coupler.

Any naphtholic coupler moiety is useful that can contain the $-CONH_2$ group in the 2- position and a coupling-off group in the 4- position and can form a compound, especially a dye, that can be washed out of the element upon oxidative coupling of the coupler. It will be appreciated that depending upon the particular developing agent and the particular type of processing, the reaction product of the coupler moiety and the oxidized developing agent can be colored or colorless. Examples of useful naphtholic coupler moieties can be unsubstituted except for the required substituents in the 2- and 4- positions as described. Optionally the naphtholic coupler moieties in addition to the substituents in the 2- and 4- positions can contain other substituents that do not adversely affect the desired properties of the element and coupler. Examples of such substituents include 5-$NHSO_2CH_3$, 5-$NHCOCH_3$ or 6-$NHSO_2CH_3$. Useful naphtholic coupler moieties include those described in, for example, the following patents in which the group described in the 2- position is replaced with $-CONH_2$, especially those having a ballasted coupling-off group: U.S. Pat. Nos. 4,840,884; 4,861,701; 2,474,293; 3,227,554; 4,482,629 and 4,857,447.

Any coupling-off group containing a ballast group known in the photographic art is useful in the 4- position of the described naphtholic coupler moiety. Examples of useful coupling-off groups are described in, for example, U.S. Pat. No. 4,861,701. Preferred coupling-off groups are those that enable release of a PUG upon photographic processing, especially those that have a releasable timing group between the bond to the coupling position of the coupler and the releasable PUG. Preferred timing groups are described in, for example, U.S. Pat. Nos. 4,861,701; 4,248,962; 4,409,323; 4,482,629 and 4,857,447.

A preferred naphtholic coupler is represented by formula:

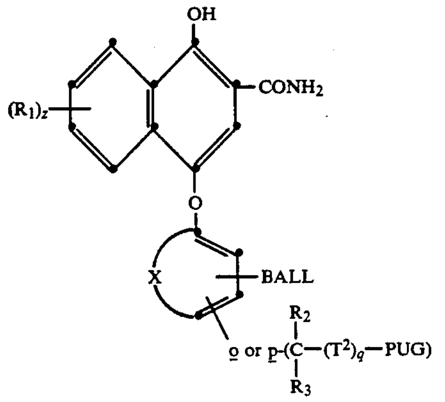

wherein

X represents the atoms completing a 5-, 6- or 7-member ring, such as an aryl or heterocyclic group;

$R_1$ is a ballast-free substituent;

z is 0, 1, 2 or 3;

BALL is a ballast group known in the photographic art;

$T^2$ is a releasable timing group, such as a timing group described in U.S. Pat. No. 5,021,322 and U.S. Pat. No. 5,026,628 of W. Begley et al.

$R_2$ and $R_3$ individually are hydrogen, unsubstituted or substituted alkyl or aryl, such as alkyl containing 1 to 40 carbon atoms or aryl containing 6 to 40 carbon atoms, such as a phenyl or naphthyl group; and, q is 0, 1 or 2.

$T^2$ is, for example, a group that enables release of PUG by means of intramolecular nucleophilic displacement, such as described in U.S. Pat. No. 4,248,962 and U.S. Pat. No. 4,861,701.

In the case of such couplers that release a PUG by means of a timing group, reaction of the coupler with oxidized color developing agent cleaves the bond between the coupler and the coupling-off group. Then the bond between the PUG and the remainder of the coupling-off group is cleaved. Bond cleavage between the PUG and the remainder of the coupling-off group preferably does not involve the action of oxidized color developing agent. The cleavage of the bond between the PUG and the remainder of the coupling-off group can involve any reaction known in the photographic art for cleavage of such groups, for example an intramolecular nucleophilic displacement reaction or other elimination reaction.

Any ballast group known in the photographic art can be useful on the coupling-off group. The ballast group (BALL) herein means an organic group of such size and configuration as to confer on the coupler molecule sufficient bulk to render the coupler substantially nondiffusible from the layer in which it is coated in a photographic element prior to exposure and processing. Representative ballast groups include substituted or unsubstituted alkyl or aryl groups containing, for example, 8 to 40 carbon atoms. Other useful ballast groups include sulfonamido groups containing 8 to 40 carbon atoms, carbonamido, carbamoyl, sulfamoyl, ester, sulfone, ether, thioether and amino groups.

A typical timing group $T^2$ is a group that enables release of a PUG by means of intramolecular nucleophilic displacement, such as described in U.S. Pat. Nos. 4,861,701; 4,857,440; 4,847,185 and 4,248,962. A preferred timing group for $T^2$ is described in U.S. Pat. No. 5,021,322 and U.S. Pat. No. 5,026,628 of W. Begley et al, the disclosures of which are incorporated herein by reference.

Illustrative timing groups $T^2$ are as follows:

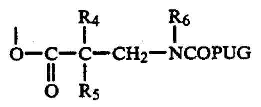

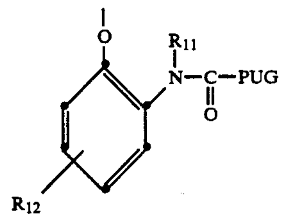

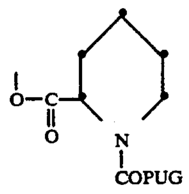

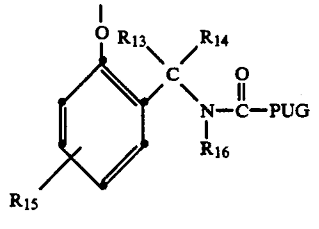

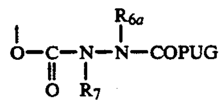

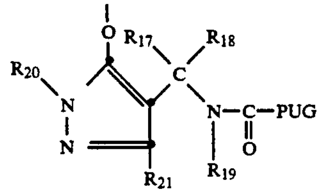

-continued

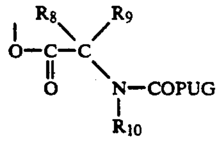 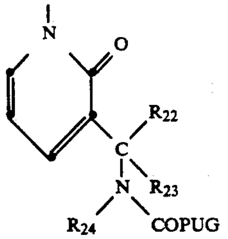

and other illustrative groups described in U.S. Pat. No. 4,857,447, the disclosures of which are incorporated herein by reference.

In the above structures, $R_4$, $R_5$, $R_6$, $R_{6a}$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ individually are hydrogen or substituents that do not adversely affect the desired properties of the naphtholic coupler or dye formed, such as unsubstituted or substituted alkyl, for example, methyl, ethyl, propyl, n-butyl, t-butyl and eicosyl, or unsubstituted or substituted aryl, such as phenyl, or substituted phenyl, and PUG is a releasable photographically useful group. At least one of the described groups on the coupling-off group is a ballast group.

As used herein the term "naphtholic coupler" refers to the entire compound including the coupler moiety and the coupling-off group. The term "naphtholic coupler moiety" herein refers to that portion of the coupler other than the coupling-off group.

The PUG is preferably any development inhibitor group that is typically made available in a photographic element in an imagewise fashion. The PUG can be a photographic reagent or a photographic dye. A photographic reagent herein is a moiety that upon release further reacts with components in the photographic element, such as a development inhibitor, a development accelerator, a bleach inhibitor, a bleach accelerator, a coupler (for example, a competing coupler, a dye-forming coupler, or a development inhibitor releasing coupler (DIR coupler)), a dye precursor, a dye, a developing agent (for example, a competing developing agent, a dye-forming developing agent, or a silver halide developing agent), a silver complexing agent, a fixing agent, an image toner, a stabilizer, a hardener, a tanning agent, a fogging agent, an ultraviolet radiation absorber, an antifoggant, a nucleator, a chemical or spectral sensitizer or a desensitizer.

The PUG can be present in the coupling-off group as a preformed species or it can be present in a blocked form or as a precursor. The PUG can be for example a preformed development inhibitor or the development inhibiting function can be blocked by being the point of attachment to the carbonyl group bonded to PUG in the coupling-off group. Other examples are a preformed dye, a dye that is blocked to shift its absorption, and a leuco dye.

A preferred naphtholic coupler as described is a photographic coupler containing a naphtholic coupler moiety and a PUG containing a hetero atom from VIb or Vb of the Periodic Table having a negative valence of 2 or 3 bonded to a carbonyl group of the coupling-off group.

Any couplers known to be useful in the photographic art can be used with the described naphtholic couplers and in various locations known in the art in a photographic element. There follows a listing of patents and publications that describe representative couplers that can be useful in combination with the described naphtholic couplers:

I. COUP's

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturübersicht," published in Agfa Mitteilungen, Band III, pp. 156–175 (1961).

Preferably such couplers are phenols and naphthols that form cyan dyes on reaction with oxidized color developing agents.

B. Couplers which form magenta dyes upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturübersicht," published in Agfa Mitteilungen, Band III, pp. 126–156 (1961).

Preferably such couplers are pyrazolones and pyrazolotriazoles that form magenta dyes upon reaction with oxidized color developing agents.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Literaturü bersicht," published in Agfa Mitteilungen, Band III, pp. 112–126 (1961).

Preferably such couplers are acylacetamides, such as benzoylacetanilides and pivaloylacetanilides that form yellow dyes upon reaction with oxidized color developing agents.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959. Preferably such couplers are cyclic carbonyl containing compounds which form colorless products on reaction with oxidized color developing agent.

Any releasable PUG known in the photographic art is useful in the coupling-off group as described. Examples of useful PUG's are as follows:

PUG's

A. PUG's which form development inhibitors upon release are described in such representative patents as U.S. Pat. Nos. 3,227,554; 3,384,657; 3,615,506; 3,617,291; 3,733,201; 4,861,701 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, oxadiazoles, benzotriazoles and benzodiazoles. Structures of preferred development inhibitor moietues are:

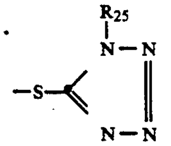

IIIA-1

-continued

IIIA-2

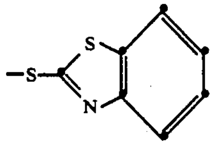

IIIA-3

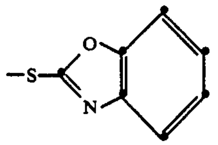

IIIA-4

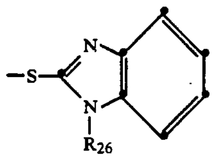

IIIA-5

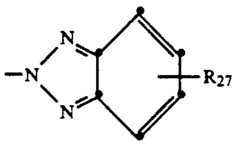

IIIA-6

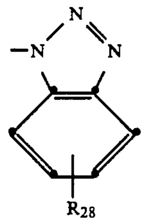

IIIA-7

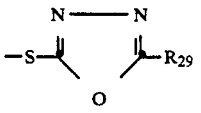

IIIA-8

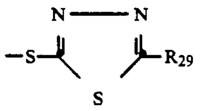

where $R_{29}$ is unsubstituted or substituted alkyl, especially alkyl containing 1 to 32 carbon atoms, such as n-butyl, t-butyl, 1-ethylpentyl, and 2-ethoxyethyl, or alkylthio, such as butylthio and octylthio; unsubstituted or substituted aryl, such as phenyl; or a heterocyclic group. $R_{25}$ and $R_{26}$ individually are hydrogen, alkyl of 1 to 8 carbon atoms such as methyl, ethyl, or butyl, phenyl or substituted phenyl; and $R_{27}$ and $R_{28}$ individually are hydrogen or one or more halogen such as chloro, fluoro or bromo; alkyl of 1 to 4 carbon atoms, carboxyl, esters, such as $-COOCH_3$, or other substituents such as $-NHCOOCH_3$, $-SO_2OCH_3$, $-OCH_2CH_2SO_2CH_3$,

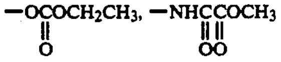

or nitro groups.

Substituents on $R_{29}$ include for example a halogen atom, a nitro group, a cyano group, an aryl group, and alkoxy group, an aryloxy group, an alkoxycarbonyl group, an aryloxcarbonyl group, a sulfamoyl group, a sulfonamido group, a carbamoyl group, an alkylsulfo group, an aryl sulfo group, a hydroxy group, an aryloxycarbonylamino group, an alkoxycarbonylamino group, an acylamino group, a ureido group, an arylthio group and an alkylthio group. When the $R_{29}$ is an aryl group the aryl group may be substituted as described for the alkyl group. When $R_{29}$ is a heterocyclic group, the heterocyclic group is a 5- or 6-membered monocyclic or condensed ring containing as a heteroatom a nitrogen atom, an oxygen atom or a sulfur atom. Examples are a pyridyl group, a quinolyl group, a furyl group, a benzothiazolyl group, an axazolyl group, an imidazolyl group, a thiazolyl group, a traizllyl group, a benzotriazolyl group, an imido group and an oxazine group.

B. PUG's which are, or form, dyes upon release:

Suitable dyes and dye precursors include azo, azomethine, azopyrazolone, indoaniline, indophenol, anthraquinone, triarylmethane, alizarin, nitro, quinoline, indigoid and phthalocyanine dyes or precursors of such dyes such as leuco dyes, tetrazolium salts or shifted dyes. These dyes can be metal complexed or metal complexable. Representative patents describing such dyes are U.S. Pat. Nos. 3,880,658; 3,931,144; 3,932,380; 3,932,381 and 3,942,987. Preferred dyes and dye precursors are azo, azomethine and indoaniline dyes and dye precursors. Structures of some preferred dyes and dye precursors are:

IIIB-1

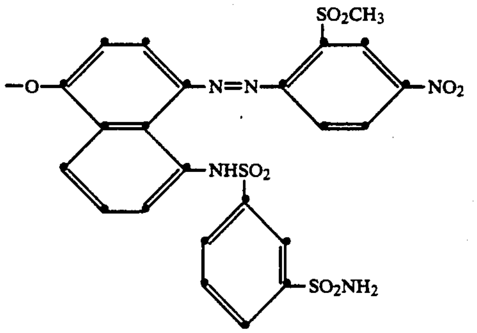

-continued

IIIB-2

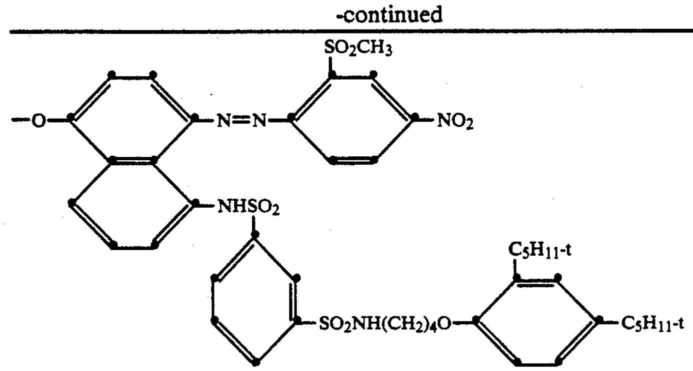

IIIB-3

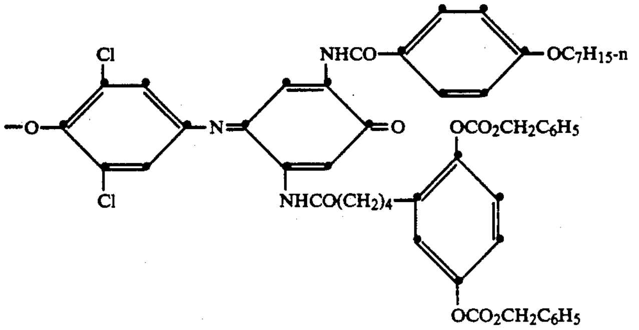

IIIB-4

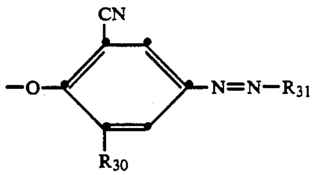

| $R_{30}$ | $R_{31}$ |
|---|---|
| —H | 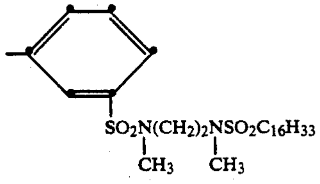 |
| —Cl | 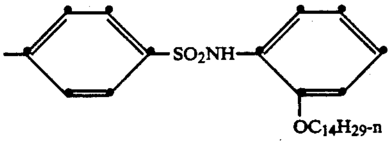 |
| —Cl | 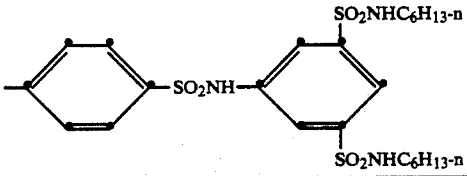 |

C. PUG's which are couplers:

Couplers released can be nondiffusible color-forming couplers, non-color forming couplers or diffusible competing couplers. Representative patents and publications describing competing couplers are: "On the Chemistry of White Couplers," by W. Püschel, Agfa-Gevaert AG Mitteilungen and der Forschungs-Laboratorium der Agfa-Gevaert AG, Springer Verlag, 1954, pp. 352-367; U.S. Pat. Nos. 2,998,314; 2,808,329; 2,689,793; 2,742,832; German Pat. No. 1,168,769 and British Pat. No. 907,274. Structures of preferred competing couplers are:

IIIC-1

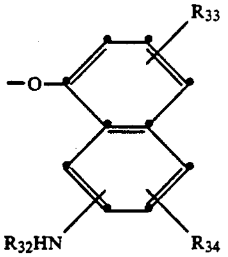

where $R_{32}$ is hydrogen or alkylcarbonyl, such as acetyl, and $R_{33}$ and $R_{34}$ are individually hydrogen or a solubilizing group, such as sulfo, aminosulfonyl, and carboxy

IIIC-2

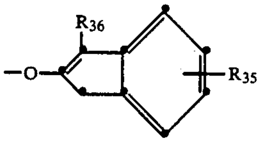

where $R_{35}$, which is the same as $R_{34}$ as defined above, and $R_{36}$ is halogen, aryloxy, arylthio, or a development inhibitor, such as a mercaptotetrazole, such as phenylmercaptotetrazole or ethylmercaptotetrazole.

D. PUG's which form developing agents:

Developing agents released can be color developing agents, black-and-white developing agents or cross-oxidizing developing agents. They include aminophenols, phenylene diamines, hydroquinones and pyrazolidones. Representative patents are: U.S. Pat. Nos. 2,193,015; 2,108,243; 2,592,364; 3,656,950; 3,658,525; 2,751,297; 2,289,367; 2,772,282; 2,743,279; 2,753,256 and 2,304,953.

Structures of preferred developing agents are:

IIID-1

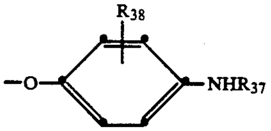

where $R_{37}$ is hydrogen or alkyl of 1 to 4 carbon atoms and $R_{38}$ is hydrogen or one or more halogen such as chloro or bromo; or alkyl of 1 to 4 carbon atoms such as methyl, ethyl or butyl groups.

IIID-2

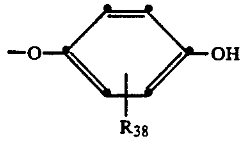

where $R_{38}$ is as defined above.

IIID-3

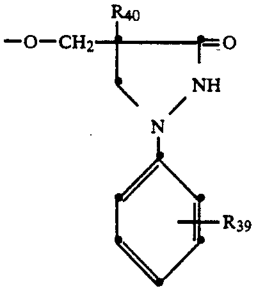

IIID-4

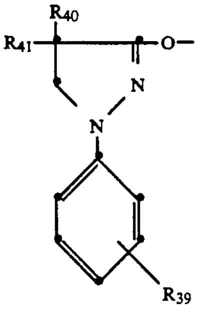

IIID-5

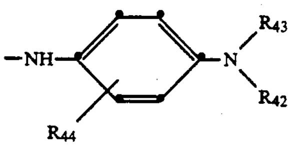

IIID-6

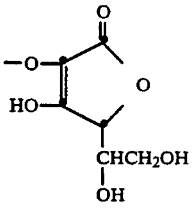

where $R_{39}$ is hydrogen or alkyl of 1 to 4 carbon atoms and $R_{40}$, $R_{41}$, $R_{42}$, $R_{43}$ and $R_{44}$ are individually hydrogen, alkyl of 1 to 4 carbon atoms such as methyl or ethyl; hydroxyalkyl of 1 to 4 carbon atoms such as hydroxymethyl or hydroxyethyl or sulfoalkyl containing 1 to 4 carbon atoms.

E. PUG's which are bleach inhibitors:

Representative patents are U.S. Pat. Nos. 3,705,801; 3,715,208; and German OLS No. 2,405,279. Structures of preferred bleach inhibitors are:

IIIE-1

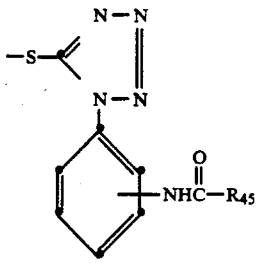

IIIE-2

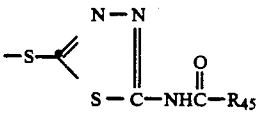

-continued

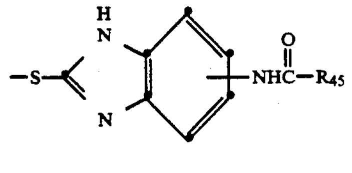

IIIE-3

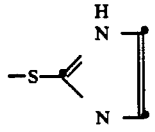

IIIE-4 where $R_{45}$ is an alkyl group of 6 to 20 carbon atoms.

F. PUG's which are bleach accelerators:

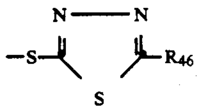

IIIF-1

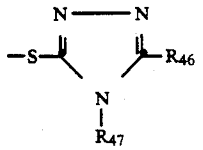

IIIF-2

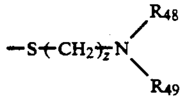

IIIF-3

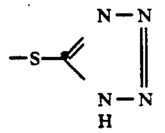

IIIF-4

$-SCH_2CH_2COOH$ IIIF-5 wherein $R_{46}$ is hydrogen, alkyl, such as ethyl and butyl, alkoxy, such as ethoxy and butoxy, or alkylthio, such as ethylthio and butylthio, for example containing 1 to 6 carbon atoms, and which may be unsubstituted or substituted; $R_{47}$ is hydrogen, alkyl or aryl, such as phenyl; $R_{48}$ and $R_{49}$ are individually alkyl, such as alkyl containing 1 to 6 carbon atoms, for example ethyl and butyl; z is 1 to 6.

The image dye-forming couplers can be incorporated in photographic elements and/or in photographic processing solutions, such as developer solutions, so that upon development of an exposed photographic element etehy will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element. For example, a layer or unit affected by PUG can be controlled by incorporating in appropriate locations in the element a scavenger layer which will confine the action of PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

It is preferred that the coupling-off group contain a releasable PUG. Depending upon the nature of the particular PUG, the couplers can be incorporated in a photographic element for different purposes and in different locations.

In the following discussion of suitable materials for use in the emulsions and elements of this invention, reference will be made to *Research Disclosure*, December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-β-(methanesulfonamido)ethylaniline sulfate hydrate; 4-amino-3-methyl-N-ethyl-N-β-hydroxyethylaniline sulfate; 4-amino-3-β-(methanesulfonamido)ethyl-N,N-diethylaniline hydrochloride; and 4-amino-N-ethyl-N-(2-methoxyethyl)-m-toluidine di-p-toluenesulfonic acid.

With negative working silver halide, the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Naphtholic couplers as described can be prepared by reactions and methods known in the organic compound synthesis art. Similar reactions and methods are described in U.S. Pat. No. 4,482,629. Typically, the naphtholic coupler is prepared by the following method:

Synthesis A:

-continued

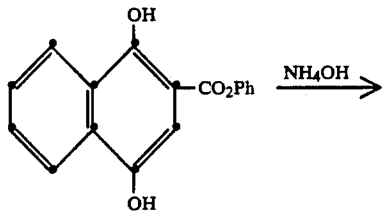

(A1)

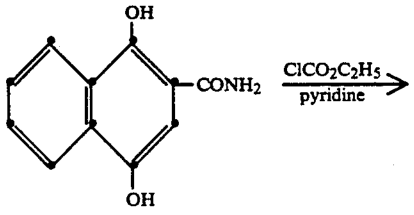

(A2)

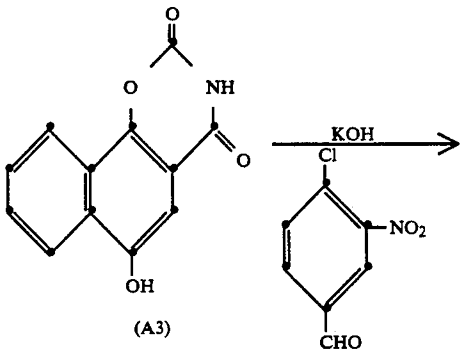

(A3)

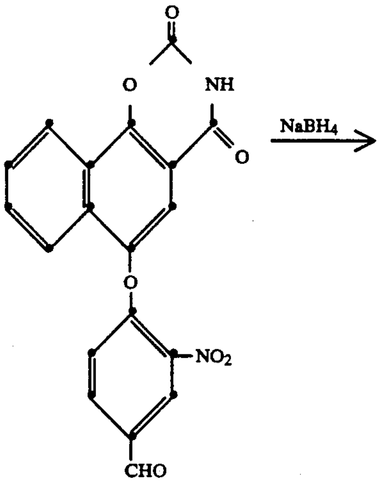

(A4)

-continued
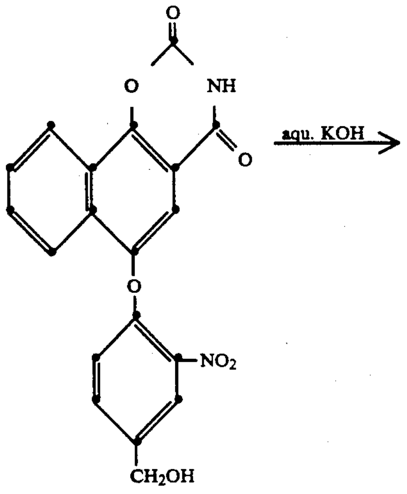
(A5)
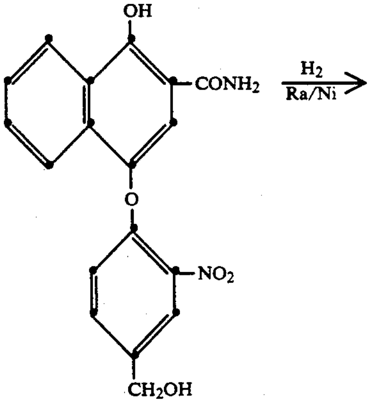
(A6)
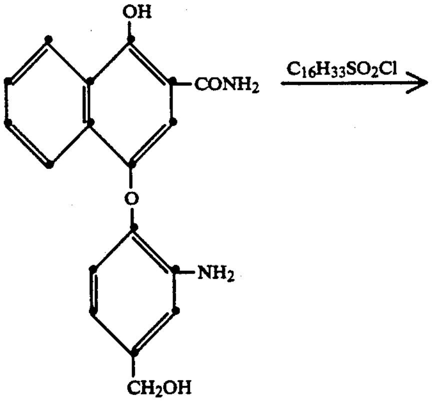
(A7)
-continued
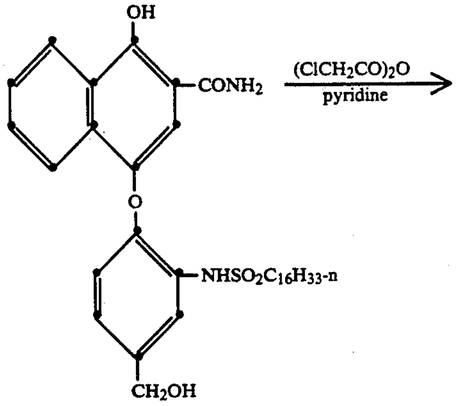
(A8)
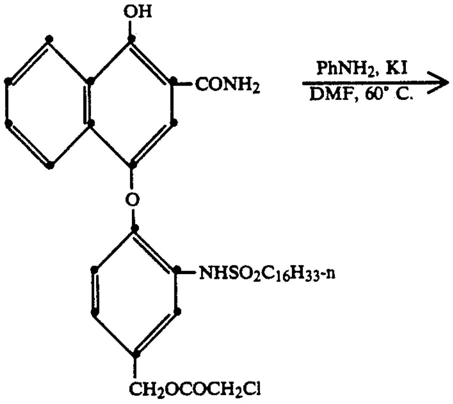
(A9)
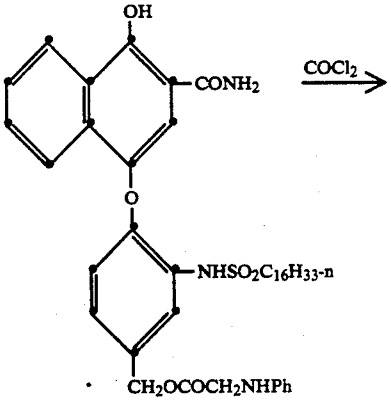
(A10)

-continued

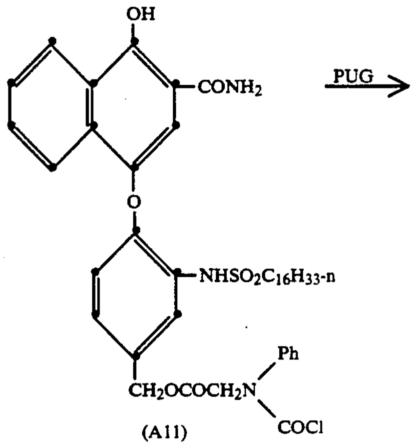

(A11)

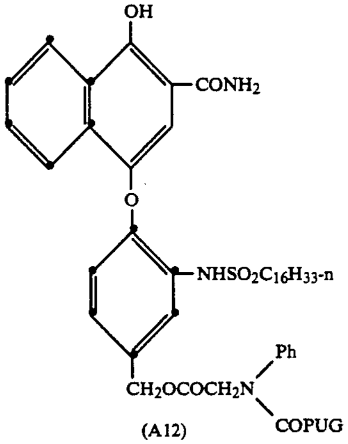

(A12)

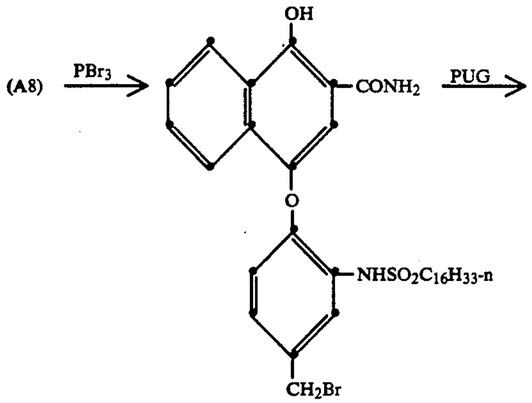

(A13)

-continued

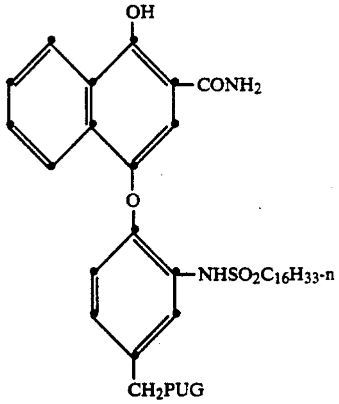

(A14)

Ph herein means phenyl.

SYNTHESIS EXAMPLE A

Compound (A2)

Phenyl-1,4-dihydroxy-2-naphthoate (100.0 g, 356.78 mmol) was dissolved in deoxygenated tetrahydrofuran (500 mL) and deoxygenated methanol (500 mL) added. To this solution, stirred at room temperature under the nitrogen atmosphere, was added ammonium acetate (50.0 g, 648.63 mmol) followed by concentrated ammonium hydroxide (1.0 L). After stirring for 3 hours the reaction was then poured into ice cold 2N—HCl (4.0 L) and enough concentrated HCl added to bring the pH to 1. The resulting product, compound (A2) was filtered off, washed well with water and air dried. The crude product was washed with dichloromethane and air dried. Yield 62.0 g (72%).

Compound (A3)

Compound (A2) (50.0 g, 0.246 mol) was dissolved in dry pyridine (150 mL) and acetonitrile (75 mL) added. The solution was stirred and cooled to −5° to 0° C. Ethyl chloroformate (50 mL, 0.523 mol) was then added dropwise with stirring while maintaining the temperature at 0° C. After the addition, the cooling bath was removed and the temperature allowed to reach room temperature. The reaction mixture was then gradually heated to reflux and the solvent allowed to distill off. This procedure was continued until the temperature had risen to approximately 120° C. and 150 mL of solvent had been collected. Heating under reflux was continued for an additional 1 hour period. The reaction mixture was then cooled to approximately 50° C. and poured into 2N—HCl, (3.0 L) held at room temperature. This suspension was then stirred for approximately 15 minutes, filtered and the residue washed well with water, acetonitrile and finally ether. This gave the product, compound (A3) sufficiently pure for the next step. Yield 43.5 g (77%).

Compound (A4)

Compound (A3) (23.0 g, 100.35 mmol) was taken up in deoxygenated dimethylsulphoxide (250 mL) and deoxygenated water (25 mL) added. To this solution, stirred at room temperature under nitrogen, was added 85% -potassium hydroxide (9.9 g, 150.53 mmol) and stirring continued until dissolution, approximately 15 minutes. 4-Chloro-3-nitrobenzaldehyde (18.62 mmol)

was then added all at once and the resulting solution stirred at 60° C. for 1 hour. The reaction mixture was then poured into ice cold 2N—HCl (2.0 L) and filtered off. The product, compound (A4), was washed with water and, while still wet, slurried in methanol, filtered and washed with ether. This product was pure enough to be used in the next step. Yield 28.0 g (74%).

Compound (A5)

Compound (A4) (28.0 g, 74.01 mmol), in a powdered form, was suspended in tetrahydrofuran (150 mL) and methanol (100 mL). Water (100 mL) was added followed by sodium borohydride (2.8 g, 74.01 mmol) in small portions. More tetrahydrofuran (50 mL) was added to aid stirring. At the end of the sodium borohydride addition complete dissolution had been achieved. The reaction was allowed to proceed for a further 15 minutes, then poured into ice cold 2N—HCl (2.0 L) and the product filtered off. The product compound (A5) was washed with methanol and while still wet with solvent, suspended in ethanol and heated to reflux. The solution was cooled, filtered, washed with methanol, ether and finally air dried. A second crop of material was obtained on concentrating the mother liquor. Total yield 19.5 g (67%).

Compound (A6)

Compound (A5) (19.0 g, 50 mmol) was suspended in water (200 mL) containing 85% -potassium hydroxide (26.34 g, 400 mmol). To this mixture was added methanol (50 mL) and then heated to 80° C. for 1 hour. The resulting dark yellow-brown solution was cooled and poured into ice cold 2N—HCl (2.0 L). The yellow product was filtered off, washed well with water and air dried. Yield 17.7 g (100%).

Compound (A7)

Compound (A6) (17.7 g, 70 mmol) was dissolved in tetrahydrofuran (80 mL) and methanol (300 mL) added. Raney-Nickel which had been washed several times with water and then methanol was added and the solution hydrogenated at 55 psi for 2 hours after which hydrogen up-take had ceased. The catalyst was filtered off, washed with methanol and the filtrate concentrated under reduced pressure to give the product, compound (A7). This product was deemed sufficiently pure to be carried on to the next step. Yield 100%.

Compound (A8)

Compound (A7) (50.0 mmol) was dissolved in dry pyridine (150 mL) and hexadecylsulfonyl chloride (16.2 g, 50.0 mmol) added. The solution was stirred at room temperature under a nitrogen atmosphere for 30 minutes. The pyridine was concentrated under reduced pressure and the residue taken up in ethyl acetate. This ethyl acetate solution was then washed with 2N—HCl (×3), dried ($MgSO_4$), filtered and concentrated. The solvent was removed under reduced pressure and the residual oil crystallized from acetonitrile. After filtering, washing with acetonitrile and drying, the yield of product compound (A8) amounted to 16.3 g (53% calculated from compound (A5)).

Compound (A9)

Compound (A8) (16.3 g, 26.6 mmol) was dissolved in tetrahydrofuran (150 mL) to which was added pyridine (3.2 mL, 39.90 mmol) followed by chloroacetic anhydride (6.82 g, 39.89 mmol) in tetrahydrofuran (30 mL) at a reasonably rapid rate. After stirring at room temperature for 30 minutes the solvent was removed under reduced pressure and the residue dissolved in ethyl acetate. The ethyl acetate solution was then washed with 2N—HCl (×2), dried ($MgSO_4$) and concentrated under reduced pressure. The residue crystallized from acetonitrile to give compound (A9) 12.2 g (66%).

Compound (A10)

Compound (A9) (12.2 g, 17.7 mmol) was dissolved in dimethylformamide (150 mL). To which was added potassium iodide (4.4 g, 25.55 mmol) and aniline (8.2 mL, 88.5 mmol) and the reaction mixture heated to 60° C. for 1.5 hours. The reaction was poured into 2N—HCl and extracted with ethyl acetate (×2). The combined ethyl acetate extracts were washed with 2N—HCl (×3), dried ($MgSO_4$), filtered and then concentrated. This residue was used as such in the next step of the reaction sequence but it could be crystallized from acetonitrile. Yield assumed to be 100%.

Compound (A11)

Compound (A10) (83.0 g, 111.26 mmol) was dissolved in tetrahydrofuran (800 mL) and the solution stirred at room temperature. N,N-4-diethylaniline (17.7 mL, 111.26 mmol) was added followed by a solution of 12% phosgene in toluene (275 mL, 333.78 mmol). The reaction mixture was stirred at room temperature for 15 minutes, concentrated under reduced pressure and the residue used as such in the next step. The yield of the product, compound (A11), was assumed to be 100%.

Compound (A12)

Compound (A11) as described above (111.26 mmol) was dissolved in dry pyridine (800 mL) and PMT (19.83 g, 111.26 mmol) added to the reaction solution. The mixture was stirred at room temperature for 1 hour. It was then concentrated under reduced pressure and the residue taken up in ethyl acetate. The ethyl acetate was washed with 2N—HCl (×3), dried ($MgSO_4$), filtered and concentrated to an oil. The oil was taken up in a mixture of ethyl acetate, dichloromethane, heptane and acetonitrile in the ratio of 20:20:56.4, respectively and subjected to flash chromatography eluting with the same solvent system to elute impurities from the column and then changed to a ratio of 27:50:20.4 to elute the product, compound (A12). The product could be recrystallized from acetonitrile. Yield 61.0 g (58%).

Calculated for $C_{50}H_{59}N_7O_8S_2$: % C=63.20, % H=6.26, % N=10.32, % S=6.75. Found: % C=63.14, % H=6.29, % N=10.23, % S=6.62.

Compound (A13)

Compound (A8) (4.0 g, 6.53 mmol) was suspended in dry ether (30 mL) and phosphorous tribromide (0.68 mL, 7.18 mmol) in ether (20 mL) added dropwise over a 15 minute period. After the addition the reaction was diluted with ether and the ether solution washed with 2N—HCl (×1), dried ($MgSO_4$), filtered and concentrated to give compound (A13). The yield was 100%.

Compound (A14)

Compound (A13) (6.53 mmol) was dissolved in dimethylformamide (40 mL) to which was added PMT (1.51 g, 7.54 mmol) and the resulting solution stirred at room temperature for 1 hour. The compound (A14) was isolated by pouring the reaction mixture into 2N—HCl and extracted with ethyl acetate (×2). The combined ethyl acetate extracts were then washed with 2N—HCl (×3), dried ($MgSO_4$), filtered and concentrated. The residue was taken up in a mixture of ethyl acetate, heptane and dichloromethane in the ratio of 15:30:5, respectively and subjected to flash chromatography eluting with the same solvent mixture. The first major band was collected to give the product. Yield 4.0 g (79%).

Calculated for $C_{41}H_{52}N_6O_5S_2$: % C=63.70, % H=6.78, % N=10.87, % S=8.30. Found: % C=63.40, % H=6.80, % N=10.76, % S=8.14.

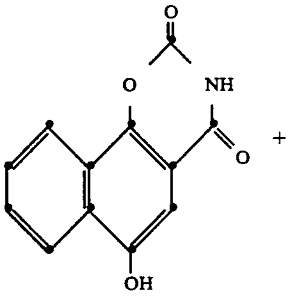

(A3)

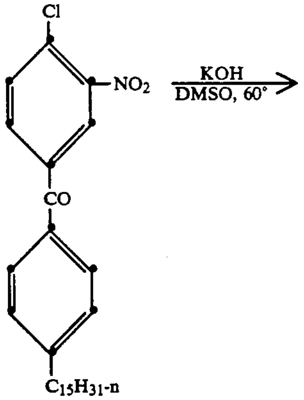

(B15)

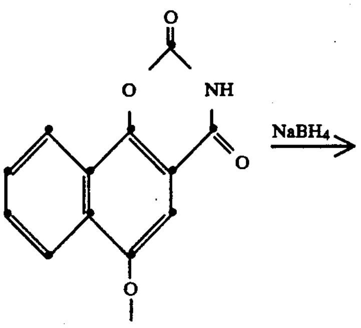

-continued

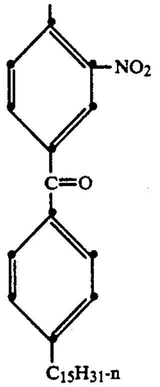

(B16)

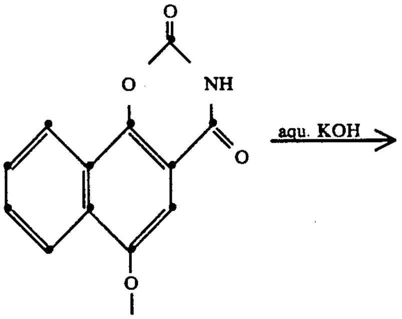

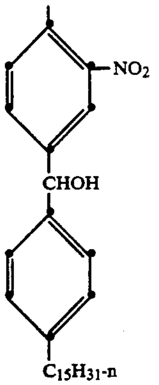

(B17)

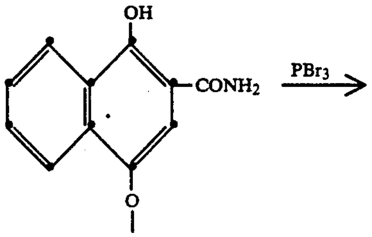

-continued

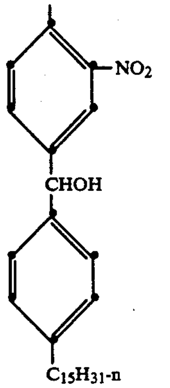

(B18)

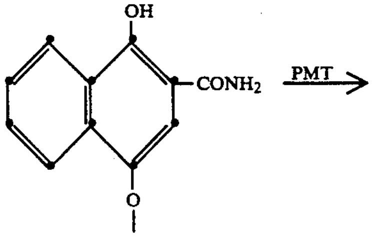

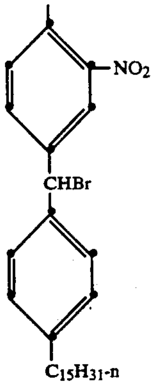

(B19)

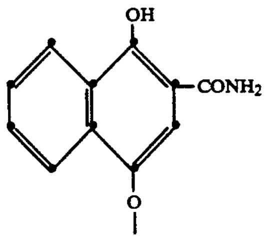

-continued

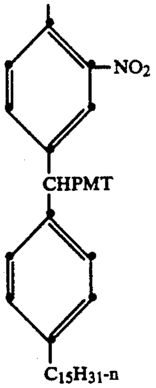

(B20)

PMT herein means phenylmercaptotetrazole.

SYNTHESIS EXAMPLE B

Compound (B16)

Compound (A3) (3.4 g, 14.83 mmol) was dissolved in deoxygenated dimethylsulphoxide (100 mL) and stirred at room temperature under a nitrogen atmosphere. To this solution was added 85%-potassium hydroxide (1.71 g, 25.95 mmol) followed by deoxygenated water (10 mL). The reaction mixture was stirred at room temperature for 15 minutes and then the benzophenone (B15) (7.0 g, 14.83 mmol) was added as a solid in a single batch. The dark colored solution was then heated to 60° C. and stirring continued for 2.5 hours. While still at 60° C. the warm solution was poured into ice cold 2N-HCl (600 mL). The yellow product was filtered off, washed with water, methanol and air dried. Yield of compound (B16) 8.8 g (89%).

Compound (B17)

Compound (B16) (8.8 g, 13.24 mmol) was dissolved in tetrahydrofuran (40 mL) to which was added methanol (20 mL) and water (20 mL). Sodium borohydride (0.5 g, 13.24 mmol) was added to the suspension portionwise with stirring. At the end of the addition dissolution was complete and the solution stirred continually for a further 15 minutes. The reaction solution was then poured into ice cold 2N-HCl (600 mL) and the product compound (B17) filtered off, washed with water, methanol and air dried. Yield 7.9 g (89%).

Compound (B18)

Compound (B17) (10.0 g, 15.0 mmol) was suspended in water (70 mL) and 85%-potassium hydroxide (7.90 g, 120.0 mmol) added together with methanol (20 mL). This mixture was stirred at 80° C. for 1 hour, cooled and poured into ice cold 2N-HCl and the mixture extracted with ethyl acetate (×2). The combined ethyl acetate extracts were then dried, ($MgSO_4$), filtered and concentrated. The residue compound (B18) was used as such in the next step of the reaction sequence. Yield (100%).

Compound (B19)

Compound (B18) (15 mmol) was dissolved in ether (70 mL) and phosphorous tribromide (1.6 mL, 16.5 mmol) in ether (15 mL) added dropwise over a period of 15 minutes. At the end of the addition the reaction solution was stirred at room temperature for a further 15 minutes. The solution was then diluted with ether, washed with 2N-HCl (×3), dried ($MgSO_4$), filtered and concentrated under reduced pressure. This gave compound (B19), sufficiently pure to be used in the next step. Yield 100%.

Compound (B20)

Compound (B19) (15.0 mmol) was dissolved in dimethylformamide (50 mL) and treated with sodium PMT (3.55 g, 17.73 mmol) while stirring at room temperature for a 1 hour period. The reaction solution was then diluted with ethyl acetate and washed with 2N-HCl (×4). The organic layer was then dried ($MgSO_4$), filtered and concentrated under reduced pressure. The oil was dissolved in 25% ethyl acetate in heptane and subjected to flash chromatography eluting with the same solvent mixture. The first major band was collected to give the product compound (B20). Yield 5.0 g [42% from compound (B17)].

Calculated for $C_{46}H_{52}N_6O_5S$: % C=68.98, % H=6.54, % N=10.49, % S=4.00. Found: % C=69.07, % H=6.44, % N=10.31, % S=4.12.

SYNTHESIS C

Compound (C-1)

Compound (A13) (20 g, 29.6 mmol) was dissolved in tetrahydrofuran (200 mL) to which was added 4-t-butyl-2-mercaptooxadiazole (4.7 g, 29.7 mmol) and triethylamine (6 g, 59.4 mmol) and the resulting solution was stirred at room temperature for 1 hour. The reaction mixture was partioned between ethyl acetate and 2N-HCl and the resulting organic layer was washed with an aqueous saturated sodium bicarbonate solution. The organic layer was dried (MgSO4) and concentrated to a thick glass. This material was dissolved in diisopropyl ether and a solid formed on standing. This material was collected and dried to give compound (C-1) M.p. 119°-121° C. The yield was 90%.

Couplers that can be prepared by these methods of synthesis include, for example:

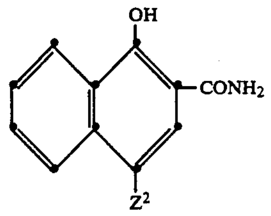

| Compound Number | $Z^2$ |
|---|---|
| 1. | 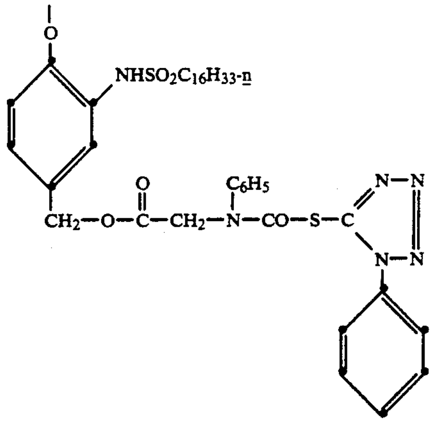 |
| 2. | 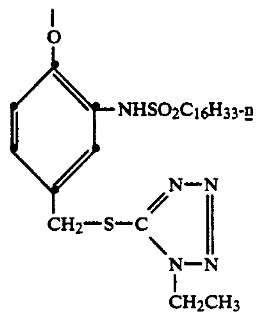 |

-continued
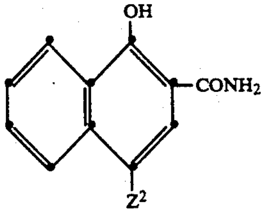
| Compound Number | $Z^2$ |
| --- | --- |
| 3. | 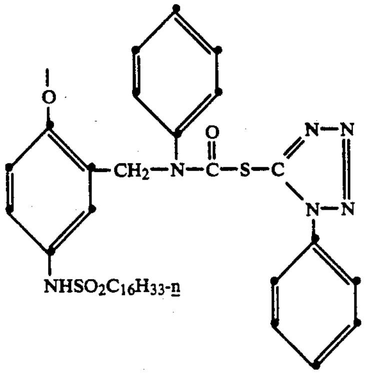 |
| 4. | 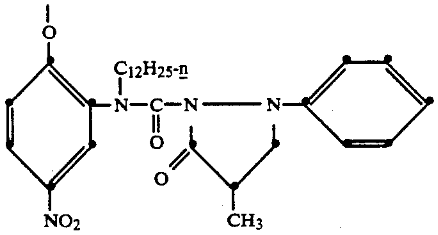 |
| 5. | 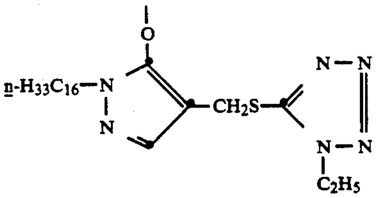 |
| 6. | 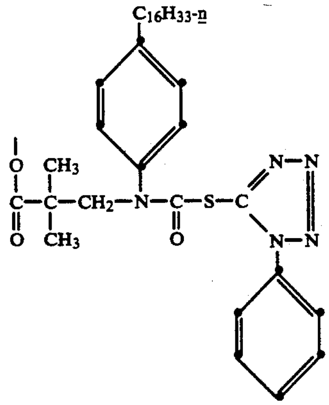 |

-continued
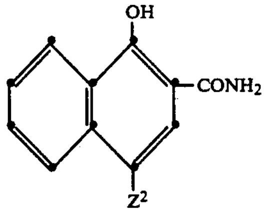
| Compound Number | $Z^2$ |
| --- | --- |
| 7. | 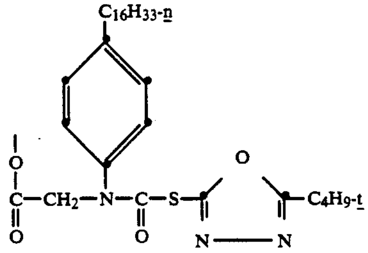 |
| 8. | 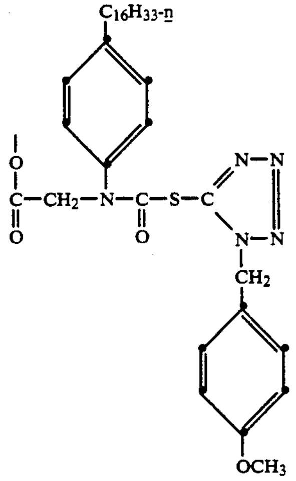 |
| 9. | 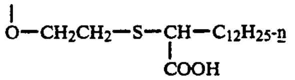 |
| 10. | 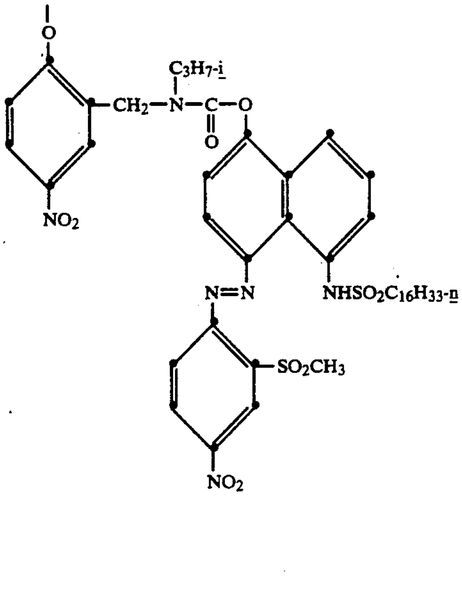 |

-continued
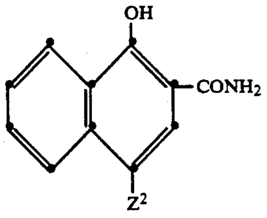
| Compound Number | $Z^2$ |
|---|---|
| 11. | 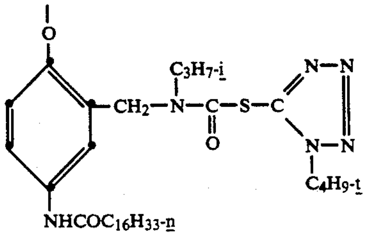 |
| 12. | 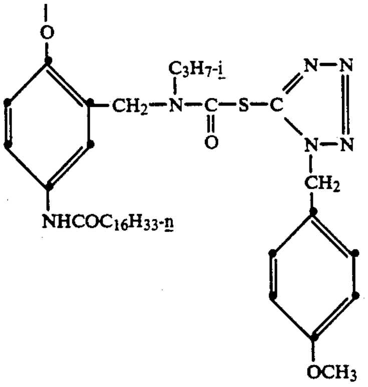 |
| 13. | 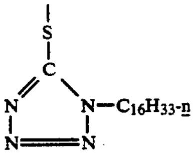 |
| 14. | 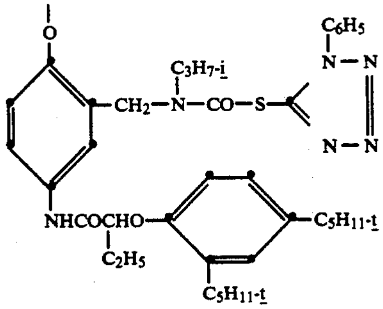 |

-continued
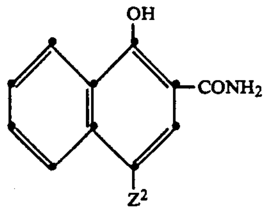
| Compound Number | $Z^2$ |
|---|---|
| 15. | 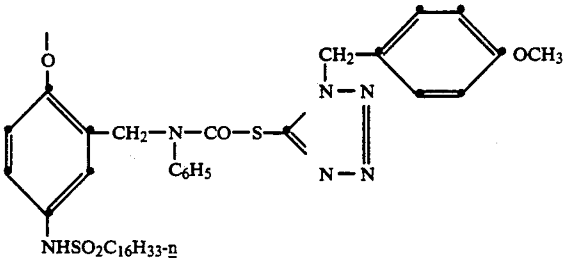 |
| 16. | 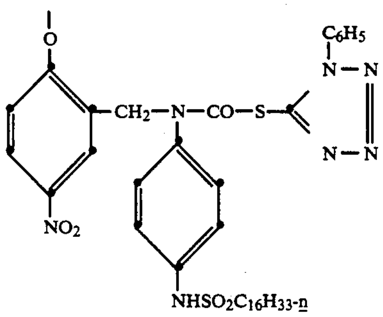 |
| 17. | 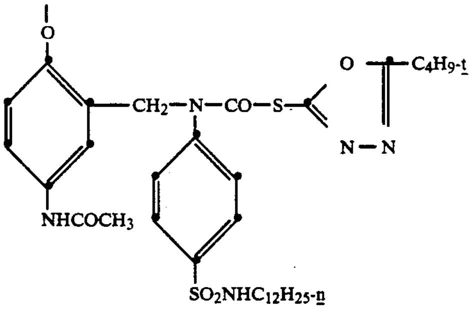 |
| 18. | 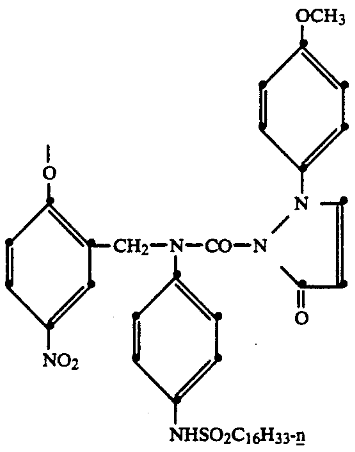 |

-continued
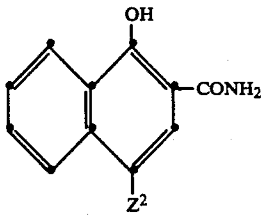
| Compound Number | $Z^2$ |
| --- | --- |
| 19. | 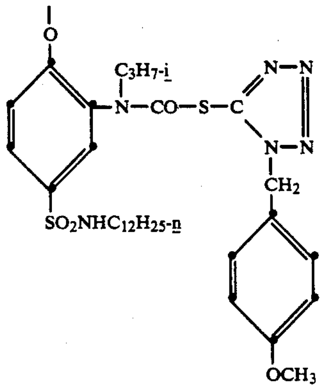 |
| 20. | 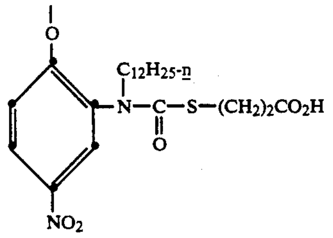 |
| 21. | 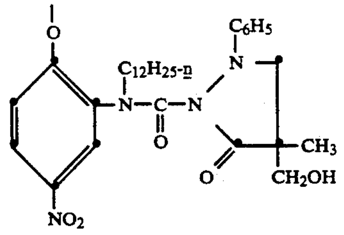 |
| 22. | 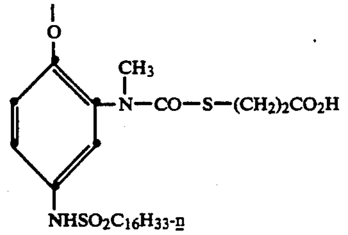 |

-continued
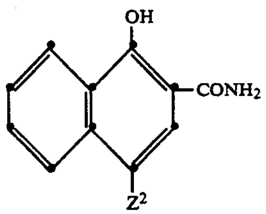
| Compound Number | $Z^2$ |
|---|---|
| 23. | 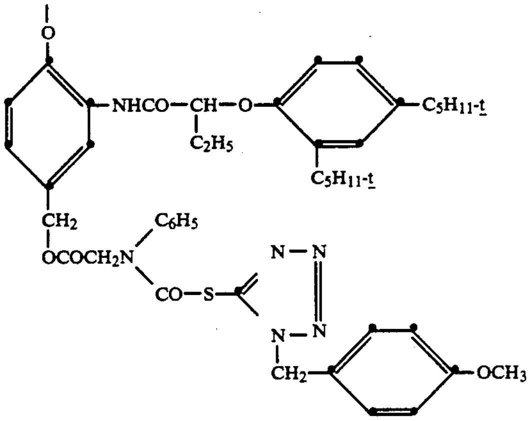 |
| 24. | 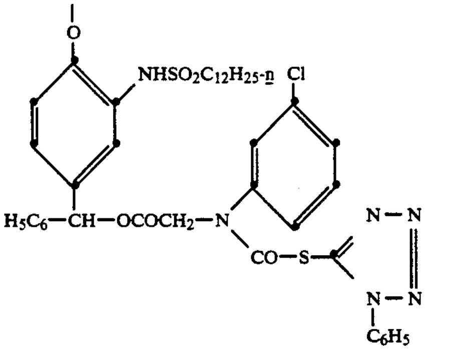 |
| 25. | 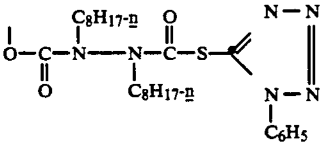 |
| 26. | 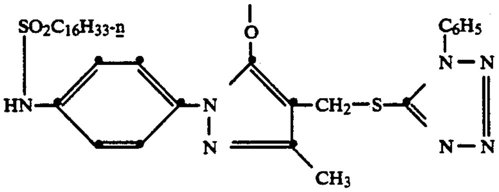 |

-continued

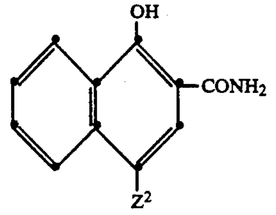

| Compound Number | $Z^2$ |
|---|---|
| 27. | 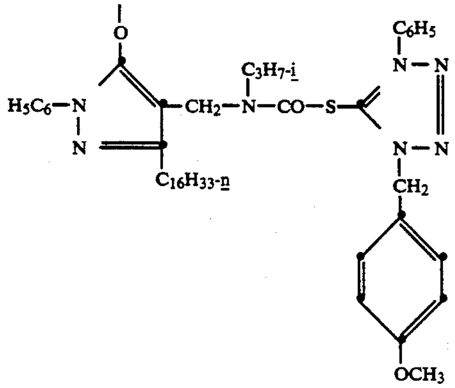 |
| 28. | 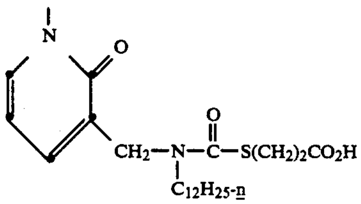 |
| 29. | 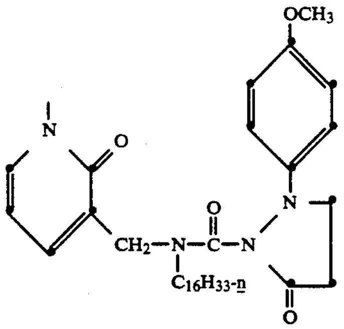 |
| 30. | 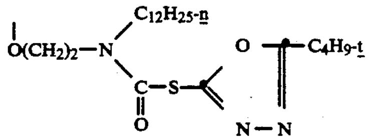 |

The following examples further illustrate the invention.

EXAMPLES 1-3

Photographic elements were prepared by coating the following layers on a cellulose ester film support (amounts of each component are indicated in mg/m$^2$):

Emulsion layer 1: Gelatin—2420; red sensitized silver bromoiodide (as Ag)—1615; yellow image coupler dispersed in dibutyl phthalate (RECEIVER LAYER).

Interlayer: Gelatin—860; didodecylhydroquinone—113.

Emulsion layer 2: Gelatin—2690; green sensitized silver bromoiodide (as Ag)—1615; magenta image coupler dispersed in tritolyl phosphate; DIR compound of Table 1 dispersed in N,N-diethyl-dodecanamide and coated at a level sufficient to provide a contrast of 0.5 (half) of the original contrast after stepwise green light exposure and processing. (CAUSER LAYER)

Protective Overcoat: Gelatin—5380; bisvinylsulfonylmethyl ether at 2% total gelatin.

Structures of the image couplers are as follows:

Magenta Image Coupler:

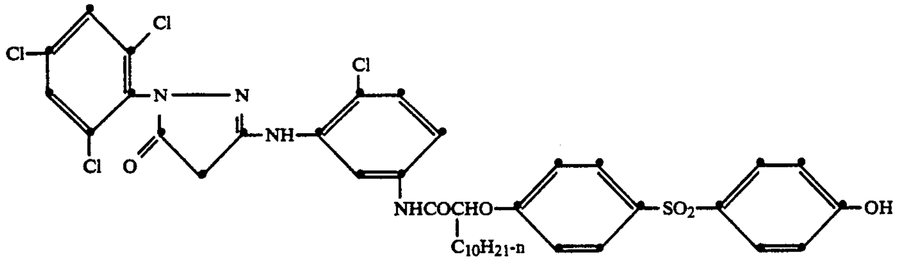

Yellow Image Coupler:

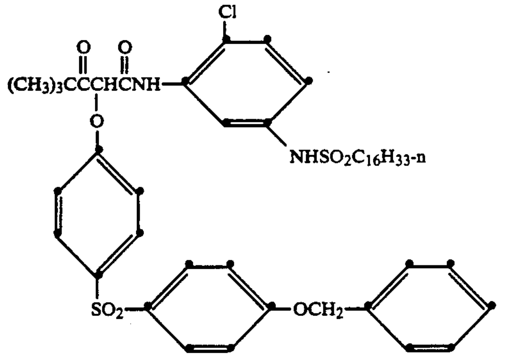

Strips of each element were exposed to green light through a graduated density step tablet, or through a 35% modulation fringe chart for sharpness measurements, and then developed 3.25 minutes at 38° C. in the following color developer, stopped, washed, bleached, fixed, washed and dried.

| Color Developer: | |
|---|---|
| Distilled water | 800 mL |
| Sodium Metabisulfite | 2.78 g |
| Sodium Sulfite. anhydrous. | 0.38 g |
| CD 4* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate (HAS) | 2.41 g |
| Diethylenetriaminepentacetic acid, pentasodium salt (40% Soln.) | 8.43 g |
| Distilled water | to 1 L |
| Adjust pH to 10.0. | |

*CD-4 is 4-amino-3-methyl-N-ethyl-N-beta-hydroxy-ethylaniline sulfate.

Processed images were read with green light to determine the contrast and AMT acutance. From plots of AMT acutance vs. the logarithm of the contrast for variations in the coated level of each development inhibitor releasing (DIR) compound, the acutance was determined at a contrast of 0.5 compared to its original contrast without the presence of the DIR compound. The acutance for the control DIR coupler was subtracted from each AMT value to provide the relative sharpness value reported as change in AMT in Table I. AMT calculations employed the following formula in which the cascaded area under the system modulation curve is shown in equation (21.104) on page 629 of the "Theory of the Photographic Process", 4th Edition, 1977, edited by T. H. James: AMT=100+66 Log [cascaded area/2.6696M] wherein th magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009-12, (1973). AMT is a further modification of CMT useful for evaluating systems which include the viewing of a positive print made from a negative.

TABLE I

| Example No./ Coupler No. | Change in AMT | Gamma Causer Gamma Receiver |
|---|---|---|
| Cntrl Cplr | 0 | 1.0 |
| 1 | 1.2 | 2.1 |
| 2 | 0 | 1.7 |
| 3 | 2.6 | 2.5 |

Control Coupler:

-continued
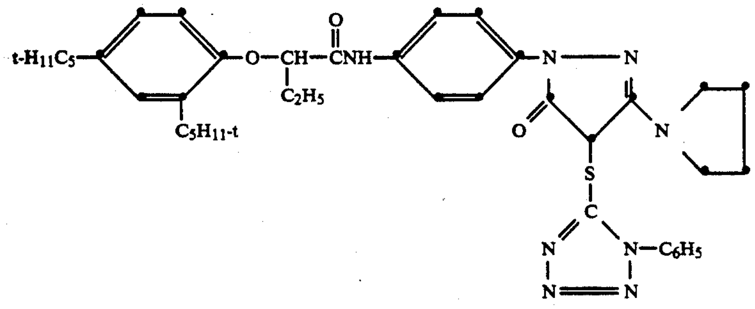
Coupler 1
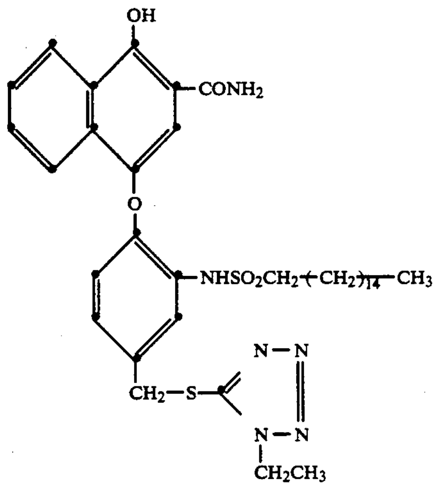
Coupler 2
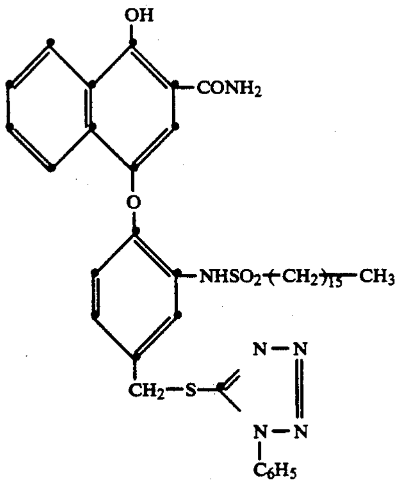
Coupler 3

-continued

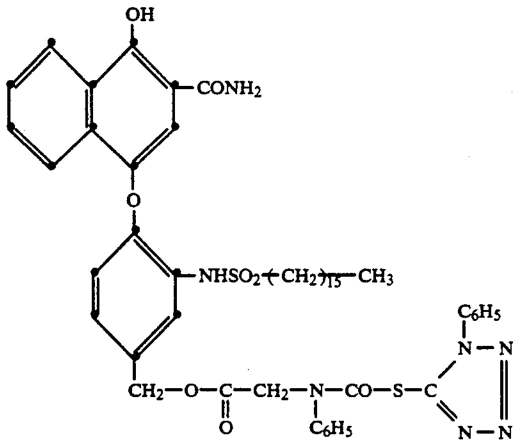

Compared to the control coupler the couplers of Examples 1-3 provide improved acutance and interimage effects.

EXAMPLE 4

A photographic film was prepared, exposed and processed like the film in Examples 1-3. The processed images were read with green light to determine the contrast. From plots of the logarithm of the contrast compared to the coated level of each DIR coupler, the reactivity was determined as the amount of DIR coupler in micromoles per square meter to reduce the contrast (gamma) to half (0.5) compared to its original contrast without the presence of the DIR coupler. The smaller the amount of the DIR compound required, the higher was the reactivity of the DIR coupler. Coupler 3 was as described in Example 3. The results are given in following Table II:

TABLE II

| Example No. | Coupler No. | Amount of DIR Coupler to Reduce Gamma in Half (Micromoles Per Square Meter) |
|---|---|---|
| 4 | 3 | 108 |
| C (Comparison) | C | 157 |
| D (Comparison) | D | 151 |

TABLE II-continued

| Example No. | Coupler No. | Amount of DIR Coupler to Reduce Gamma in Half (Micromoles Per Square Meter) |
|---|---|---|
| Coupler C | | |

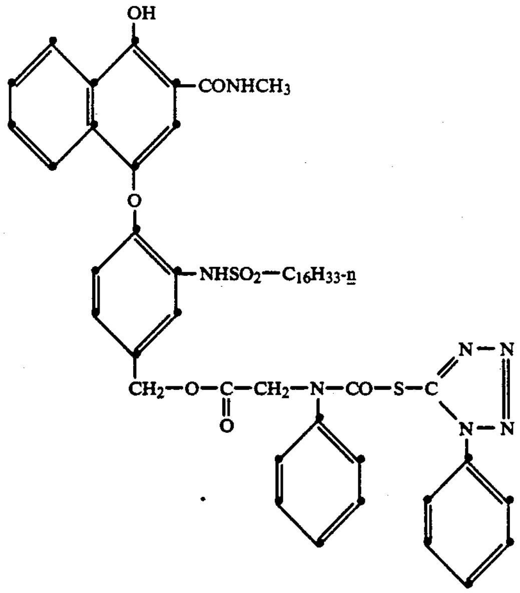

TABLE II-continued

| Example No. | Coupler No. | Amount of DIR Coupler to Reduce Gamma in Half (Micro-moles Per Square Meter) |
|---|---|---|
| Coupler D<br>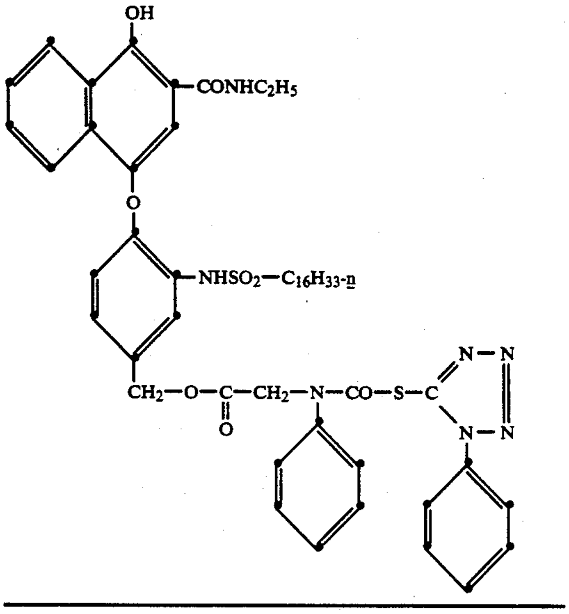 | | |

The invention has been described in detail with particular reference to preferred embodiments thereof, but it will be understood that variations and modifications can be effected within the spirit and scope of the invention.

What is claimed is:

1. A photographic naphtholic coupler comprising a ballast-free naphtholic coupler moiety containing a $-CONH_2$ group in the 2-position and in the 4-position a ballast coupling-off group that comprises a releasable inhibitor group, the coupler represented by the structure:

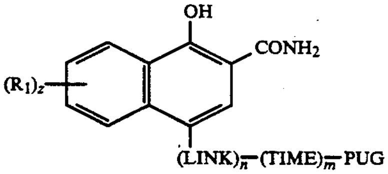

wherein $R_1$ is a ballast-free substituent;

z is 0, 1, 2 or 3;

TIME is a timing group capable of being released from the LINK moiety upon photographic processing of a photographic element containing the coupler;

n and m individually are 0, 1, or 2;

LINK is a linking group capable of being released from the naphtholic coupler upon oxidative coupling of the naphtholic coupler;

PUG is a releasable development inhibitor group; and at least one of n and m is 1 or 2.

2. A photographic coupler as in claim 1 wherein the releasable development inhibitor group is a mercaptotetrazole, mercaptooxadiazole, or mercaptothiadiazole group.

3. A photographic coupler that is

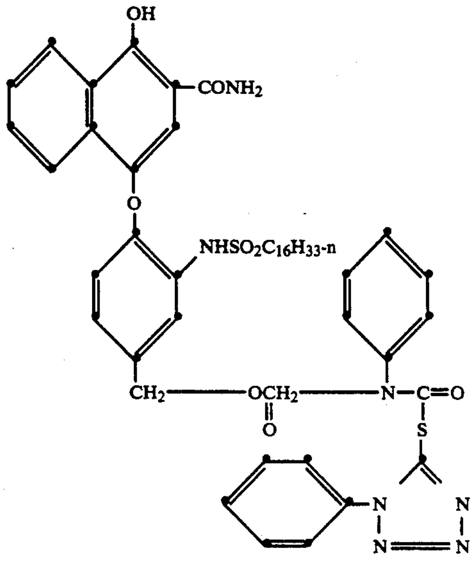

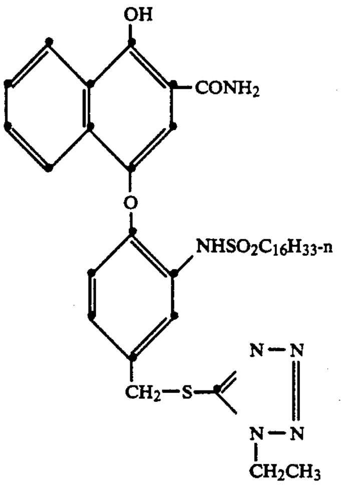

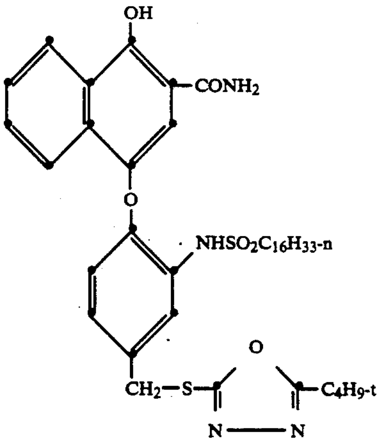

or

-continued

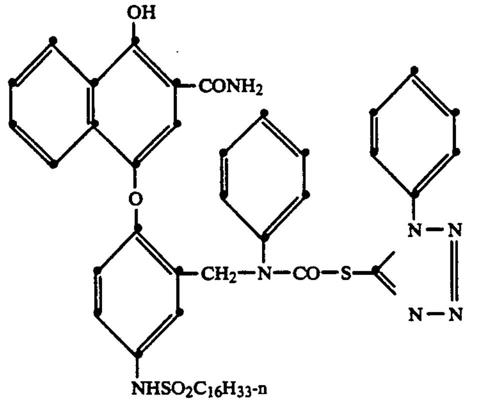

4. A photographic naphtholic coupler comprising a ballast-free naphtholic coupler moiety containing a $-CONH_2$ group in the 2-position and in the 4-position a ballast coupling-off group that comprises a releasable inhibitor group, the coupler represented by the structure:

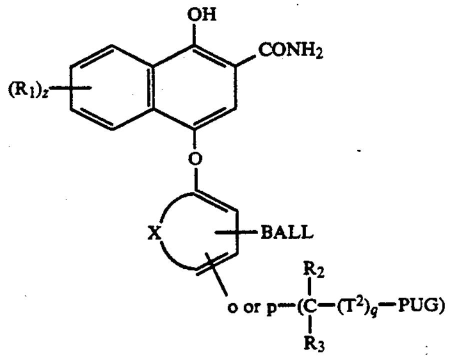

wherein

X represents the atoms completing a 5-, 6 or 7-member aryl or heterocyclic group;

BALL is a ballast group;

$T^2$ is a releasable timing group;

$R_2$ and $R_3$ individually are hydrogen, unsubstituted or substituted alkyl or aryl;

q is 0, 1 or 2; and

PUG is a releasable photographically useful group.

* * * * *